United States Patent
Morishima et al.

(10) Patent No.: US 12,427,223 B2
(45) Date of Patent: Sep. 30, 2025

(54) DEODORANT COMPOSITION, ABSORBENT, AND ABSORBENT ARTICLE

(71) Applicant: SUMITOMO SEIKA CHEMICALS CO., LTD., Hyogo (JP)

(72) Inventors: Shota Morishima, Himeji (JP); Moe Nishida, Himeji (JP)

(73) Assignee: SUMITOMO SEIKA CHEMICALS CO., LTD., Hyogo (JP)

(*) Notice: Subject to any disclaimer, the term of this patent is extended or adjusted under 35 U.S.C. 154(b) by 418 days.

(21) Appl. No.: 17/768,361

(22) PCT Filed: Oct. 14, 2020

(86) PCT No.: PCT/JP2020/038759
§ 371 (c)(1),
(2) Date: Apr. 12, 2022

(87) PCT Pub. No.: WO2021/075458
PCT Pub. Date: Apr. 22, 2021

(65) Prior Publication Data
US 2024/0123111 A1    Apr. 18, 2024

(30) Foreign Application Priority Data
Oct. 18, 2019  (JP) .................................. 2019-191299

(51) Int. Cl.
A61L 15/46 (2006.01)
A61L 15/18 (2006.01)
A61L 15/24 (2006.01)
B01J 20/18 (2006.01)
B01J 20/26 (2006.01)

(52) U.S. Cl.
CPC ............. *A61L 15/46* (2013.01); *A61L 15/18* (2013.01); *A61L 15/24* (2013.01); *B01J 20/18* (2013.01); *B01J 20/261* (2013.01); *A61L 2300/104* (2013.01)

(58) Field of Classification Search
None
See application file for complete search history.

(56) References Cited

U.S. PATENT DOCUMENTS

| | | | |
|---|---|---|---|
| 6,277,772 B1 | 8/2001 | Gancet et al. | |
| 2006/0189953 A1* | 8/2006 | Taniguchi | A61F 13/8405 521/50 |
| 2015/0252130 A1 | 9/2015 | Loick et al. | |
| 2016/0074550 A1 | 3/2016 | Loick et al. | |

FOREIGN PATENT DOCUMENTS

| | | |
|---|---|---|
| EP | 1616911 | 1/2006 |
| EP | 1779727 | 5/2007 |
| EP | 2095943 | 9/2009 |
| EP | 3410112 | 12/2018 |
| JP | S59-179114 | 10/1984 |
| JP | S61-186502 | 8/1986 |
| JP | S63-267433 | 11/1988 |
| JP | H8-027372 | 1/1996 |
| JP | 2001-505237 | 4/2001 |
| JP | 2004-346089 | 12/2004 |
| JP | 2005-194376 | 7/2005 |
| JP | 2006-052205 | 2/2006 |
| JP | 2008-174730 | 7/2008 |
| JP | 2010-094656 | 4/2010 |
| JP | 2013-070820 | 4/2013 |
| JP | 2014-023949 | 2/2014 |
| WO | 98/020915 | 5/1998 |
| WO | 2021/006178 | 1/2021 |

OTHER PUBLICATIONS

International Search Report of PCT/JP2020/038759, Dec. 28, 2020, 2 pages.
Chen Chang Ming, "Formulation Process and Principle Analysis of Fine Chemicals", Beijing Industrial University Press, 2002, p. 414-p. 415; Partial translation provided.
International Preliminary Report on Patentability of PCT/JP2020/038759, Apr. 28, 2022, 6 pages.

* cited by examiner

*Primary Examiner* — David J Blanchard
*Assistant Examiner* — Daniel F Coughlin
(74) *Attorney, Agent, or Firm* — HSML P.C.

(57) ABSTRACT

An absorbent article 100 includes an absorber 10, the absorber 10 contains water-absorbent resin particle 10a composed of a deodorant composition, and the deodorant composition contains silver zeolite, a sulfur compound, and a water-absorbent resin.

18 Claims, 1 Drawing Sheet

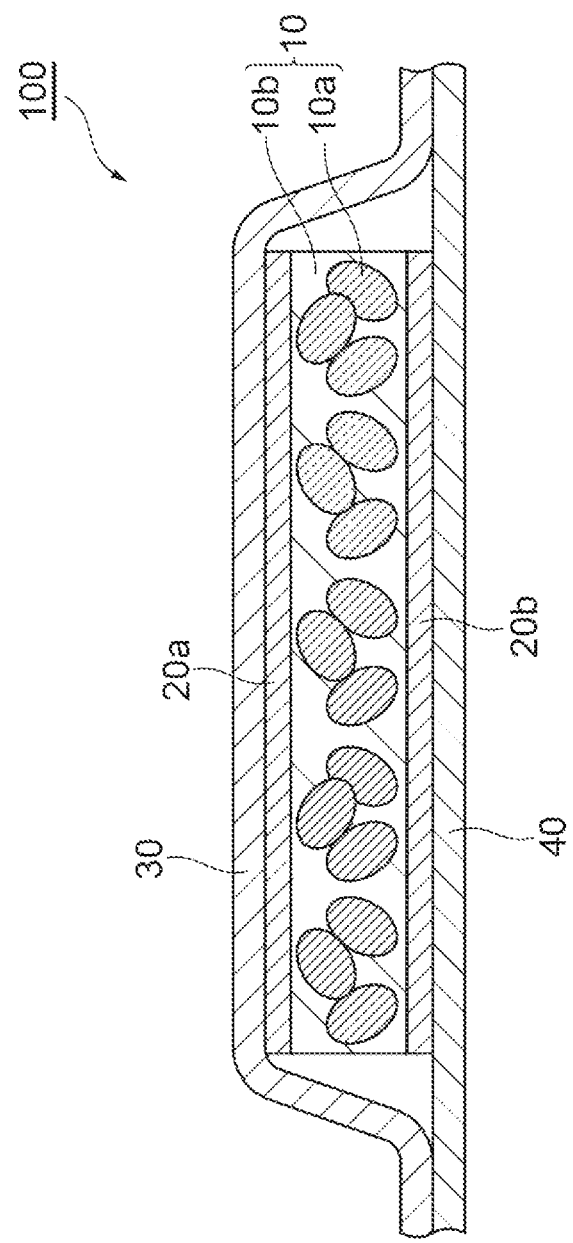

DEODORANT COMPOSITION, ABSORBENT, AND ABSORBENT ARTICLE

TECHNICAL FIELD

The present invention relates to a deodorant composition, an absorber, and an absorbent article.

BACKGROUND ART

Absorbent articles for absorbing various liquids are used in various uses such as diapers, sanitary materials, agricultural and horticultural materials, and industrial materials. When an absorbent article absorbs a liquid (for example, a body fluid such as urine, blood, or sweat), there is a case where an odor is generated. There is a case where a deodorant component such as a zeolite is used to suppress the generation of an odor (for example, refer to Patent Literature 1 below).

CITATION LIST

Patent Literature

[Patent Literature 1] Japanese Unexamined Patent Publication No. S59-179114

SUMMARY OF INVENTION

Technical Problem

There is a case where silver zeolite is used as the zeolite for the purpose of imparting deodorant performance to absorbent articles. However, for absorbent articles in which silver zeolite is used, there is a demand for improving the deodorant performance.

An object of one aspect of the present invention is to provide a deodorant composition capable of improving deodorant performance in the case of using silver zeolite. An object of another aspect of the present invention is to provide an absorber and an absorbent article in which the deodorant composition is used.

Solution to Problem

The present inventors found that, when silver zeolite and a sulfur compound are jointly used, deodorant performance is improved in the case of using silver zeolite.

A first embodiment of one aspect of the present invention provides a deodorant composition that is used in an absorbent article and contains silver zeolite and a sulfur compound.

According to the deodorant composition of the first embodiment, it is possible to improve the deodorant performance in the case of using silver zeolite.

When the deodorant composition is colored before absorbing a liquid, problems such as deterioration of the liquid absorption performance of the deodorant composition and degradation of the commercial value may be caused. Therefore, there is a demand for suppressing the coloring of the deodorant composition, and in particular, there is a demand for suppressing yellowing of the deodorant composition over time in the case of using silver zeolite.

With respect to this, the present inventors found that, when silver zeolite is used as a deodorant component in a deodorant composition containing a water-absorbent resin, the deodorant performance is improved compared with that in a case where a deodorant component is not used, but the deodorant composition turns yellow over time (refer to Reference Example A1 described below). With respect to this, the present inventors found that, when silver zeolite and a sulfur compound are jointly used, it is possible to suppress yellowing of the deodorant composition over time while improving the deodorant performance in the case of using silver zeolite.

A second embodiment of one aspect of the present invention provides a deodorant composition containing silver zeolite, a sulfur compound, and a water-absorbent resin.

According to the deodorant composition of the second embodiment, it is possible to suppress yellowing of the deodorant composition over time while improving the deodorant performance in the case of using silver zeolite.

Another aspect of the present invention provides an absorber containing the above-mentioned deodorant composition.

Still another aspect of the present invention provides an absorbent article including the above-mentioned absorber.

Advantageous Effects of Invention

According to one aspect of the present invention, it is possible to provide a deodorant composition capable of improving deodorant performance in the case of using silver zeolite. According to another aspect of the present invention, it is possible to provide an absorber and an absorbent article in which the deodorant composition is used.

BRIEF DESCRIPTION OF DRAWING

FIG. 1 is a cross-sectional view showing an example of an absorbent article.

DESCRIPTION OF EMBODIMENTS

Hereinafter, embodiments of the present invention will be described in detail. However, the present invention is not limited to the following embodiments, and can be variously modified and implemented within the scope of the gist thereof.

In the present specification, "acrylic" and "methacrylic" are collectively referred to as "(meth)acrylic." "Acrylate" and "methacrylate" are also referred to as "(meth)acrylate." Regarding numerical value ranges described in stages in the present specification, an upper limit value or a lower limit value of a numerical value range in a certain stage can be optionally combined with an upper limit value or a lower limit value of a numerical value range in another stage. In a numerical value range described in the present specification, an upper limit value or a lower limit value of the numerical value range may be replaced with a value shown in Examples. For materials exemplified in the present specification, one kind may be used alone, or two or more kinds may be used in combination. In a case where there are a plurality of substances corresponding to each of components in a composition, a content of each of the components in the composition means a total amount of the plurality of substances present in the composition unless otherwise specified. "Physiological saline" refers to an aqueous solution of 0.9% by mass sodium chloride. "Room temperature" means 25° C.±2° C.

A deodorant composition of a first embodiment is a deodorant composition that is used in an absorbent article and contains silver zeolite and a sulfur compound. According to the deodorant composition of the first embodiment, it is possible to improve the deodorant performance in the case of using silver zeolite. According to the deodorant composition of the first embodiment, it is possible to improve the deodorant performance when the deodorant composition absorbs water in an absorbent article. The sulfur compound has a deodorant action different from a urease inhibitory action, and it is presumed that the deodorant performance is improved by a synergistic effect of this deodorant action of the sulfur compound and the urease inhibitory action of silver in the silver zeolite. However, the reason is not limited to this content.

The positional location of the deodorant composition of the first embodiment in an absorbent article is not particularly limited. The deodorant composition of the first embodiment may be disposed at an arbitrary location of an absorbent article or may be included in an arbitrary constituent member of an absorbent article. For example, the deodorant composition of the first embodiment may be included in an absorber of an absorbent article, may be contained in a constituent member other than the absorber of the absorbent article, or may be present between constituent members of the absorbent article. According to the deodorant composition of the first embodiment, it is possible to improve the deodorant performance in the case of using silver zeolite even in a location where a water-absorbent resin is not present in an absorbent article.

Body fluids such as urine, blood, and sweat are likely to generate an odor. Therefore, absorbent articles that are supposed to absorb body fluids (diapers, toilet training pants, incontinence pads, sanitary materials, and the like) are required to be better in terms of the deodorant performance. With respect to this, according to the deodorant composition of the first embodiment, it is possible to improve the deodorant performance when the deodorant composition absorbs body fluids in an absorbent article.

A deodorant composition of a second embodiment contains silver zeolite, a sulfur compound, and a water-absorbent resin. The deodorant composition of the second embodiment may be a deodorant composition corresponding to the deodorant composition of the first embodiment. According to the deodorant composition of the second embodiment, it is possible to suppress yellowing of the deodorant composition over time while improving the deodorant performance in the case of using silver zeolite. According to the deodorant composition of the second embodiment, it is possible to improve the deodorant performance when the deodorant composition absorbs water. It is presumed that the reason for the improvement in the deodorant performance is the same as the above-mentioned reason regarding the first embodiment. However, the reason is not limited to this content. According to the deodorant composition of the second embodiment, it is possible to improve the deodorant performance when the deodorant composition absorbs body fluids in an absorbent article.

According to the deodorant composition of the second embodiment, it is possible to suppress yellowing of the deodorant composition over time in at least one of short-term storage and long-term storage. As a yellowing suppression effect in short-term storage, according to the deodorant composition of the second embodiment, it is possible to suppress yellowing when 1 day (24 hours) has elapsed from the preparation of the deodorant composition by mixing silver zeolite, a sulfur compound, and a water-absorbent resin (for example, it is possible to suppress yellowing when the deodorant composition is retained at a temperature of 70±2° C. and a relative humidity of 90±2% and 1 day (24 hours) has elapsed). Furthermore, according to the deodorant composition of the second embodiment, it is also possible to suppress yellowing when 3 days (72 hours) has elapsed from the preparation of the deodorant composition by mixing silver zeolite, a sulfur compound, and a water-absorbent resin (for example, it is also possible to suppress yellowing when the deodorant composition is retained at a temperature of 70±2° C. and a relative humidity of 90±2% and 3 days (72 hours) has elapsed). As a yellowing suppression effect in long-term storage, according to the deodorant composition of the second embodiment, it is possible to suppress yellowing when 14 days (336 hours) has elapsed from the preparation of the deodorant composition by mixing silver zeolite, a sulfur compound, and a water-absorbent resin (for example, it is possible to suppress yellowing when the deodorant composition is retained at a temperature of 70±2° C. and a relative humidity of 90±2% and 14 days (336 hours) has elapsed). According to the deodorant composition of the second embodiment, it is possible to suppress yellowing of the deodorant composition over time before water absorption. It is presumed that, although silver ions contained in the silver zeolite may act as a cause of yellowing, the sulfur compound acts on the silver ions (for example, the sulfur compound forms a salt with the silver ions), whereby yellowing is suppressed. However, the reason is not limited to this content.

In the deodorant composition of the present embodiment (including the deodorant composition of the first embodiment and the deodorant composition of the second embodiment, which will be the same below), in a case where the deodorant composition contains a water-absorbent resin, the amount of ammonia generated, which is measured in the following procedures (A1) to (A3), may be 1500 ppm or less, 1200 ppm or less, 1000 ppm or less, 800 ppm or less, 500 ppm or less, 450 ppm or less, 400 ppm or less, 200 ppm or less, 100 ppm or less, 50 ppm or less, 30 ppm or less, 10 ppm or less, 5 ppm or less, 3 ppm or less, 2 ppm or less, or 1 ppm or less.

(A1) 25.0 g of urea, 9.0 g of sodium chloride, 0.6 g of magnesium sulfate heptahydrate, 0.7 g of calcium lactate, 4.0 g of potassium sulfate, 2.5 g of ammonium sulfate, and water (for example, distilled water) are mixed to obtain 1000 g of an aqueous solution.

(A2) 30.0 g of the aqueous solution and 1.0 mL of a 10 U/mL urease aqueous solution are mixed to obtain a test solution.

(A3) After 1.0 g of the deodorant composition is swollen with the test solution (a liquid mixture of 30.0 g of the above-mentioned aqueous solution and 1.0 mL of the urease aqueous solution), the amount of ammonia generated when 24 hours has elapsed (24 hours has elapsed from the swelling) at a temperature of 35±2° C. is measured.

The deodorant composition swollen in (A3) can be retained for 24 hours in, for example, 900 mL of a dry air enclosed in a 2 L bag. The bag enclosing the swollen deodorant composition can be retained at, for example, a temperature of 35±2° C. and a relative humidity of 60±2%. As the deodorant composition, a water-absorbent resin composition containing silver zeolite, a sulfur compound, and a water-absorbent resin, in which, based on the total mass of the water-absorbent resin, the content of silver zeolite is 500 ppm, the content of the sulfur compound is 1000 ppm, and the remainder is composed of the water-absorbent resin can be used.

In the deodorant composition of the first embodiment, the amount of ammonia generated, which is measured in the following procedures (B1) to (B3), may be 2500 ppm or less, 2000 ppm or less, 1500 ppm or less, 1200 ppm or less, 1100 ppm or less, 1000 ppm or less, 800 ppm or less, 700 ppm or less, 600 ppm or less, 500 ppm or less, 300 ppm or less, or 200 ppm or less.

(B1) 25.0 g of urea, 9.0 g of sodium chloride, 0.6 g of magnesium sulfate heptahydrate, 0.7 g of calcium lactate, 4.0 g of potassium sulfate, 2.5 g of ammonium sulfate, and water (for example, distilled water) are mixed to obtain 1000 g of an aqueous solution.

(B2) 30.0 g of the aqueous solution and 1.0 mL of a 30 U/mL urease aqueous solution are mixed to obtain a test solution.

(B3) After the test solution (a liquid mixture of 30.0 g of the above-mentioned aqueous solution and 1.0 mL of the urease aqueous solution) is permeated into entire fluff pulp in an absorber obtained by dispersing 1.875 g of fluff pulp, 0.001 g of silver zeolite, 0.005 g of a sulfur compound, and 0.625 g of fluff pulp in order, the amount of ammonia generated when 24 hours has elapsed (24 hours has elapsed from the permeation) at a temperature of 35±2° C. is measured.

The absorber in (B3) can be retained for 24 hours in, for example, 900 mL of a dry air enclosed in a 2 L bag. The bag enclosing the absorber can be retained at, for example, a temperature of 35±2° C. and a relative humidity of 60±2%.

The deodorant composition of the present embodiment may be in the form of particles. The deodorant composition of the present embodiment is capable of absorbing liquid containing water as a main component (for example, body fluids such as urine, blood, and sweat). The deodorant composition of the present embodiment can be used as a constituent component of an absorber. The present embodiment can be used in, for example, diapers (for example, paper diapers), toilet training pants, incontinence pads, sanitary materials (sanitary products and the like), sweat pads, pet sheets, portal toilet members, animal excrement treatment materials, agricultural and horticultural materials (water retention agents, soil improvement agents, and the like), industrial materials (waterproofing agents, dew condensation inhibitors and the like) and the like.

The deodorant composition of the present embodiment may be a water-absorbent resin composition containing a water-absorbent resin or may not contain a water-absorbent resin. That is, the deodorant composition of the first embodiment may contain a water-absorbent resin or may not contain a water-absorbent resin. The deodorant composition of the second embodiment is a water-absorbent resin composition containing a water-absorbent resin. The water-absorbent resin may be in the form of particles. The water-absorbent resin preferably has a structural unit derived from an ethylenically unsaturated monomer from the viewpoint of easily improving the deodorant performance and the viewpoint of easily suppressing yellowing over time. The water-absorbent resin having a structural unit derived from an ethylenically unsaturated monomer can be obtained by polymerizing a monomer composition containing an ethylenically unsaturated monomer. A method for polymerizing a water-absorbent resin is not particularly limited and examples thereof include a reverse phase suspension polymerization method, an aqueous solution polymerization method, a bulk polymerization method, and a precipitation polymerization method. The water-absorbent resin may be a crosslinking polymer.

Examples of the ethylenically unsaturated monomer include a carboxylic acid-based monomer such as α,β-unsaturated carboxylic acid such as (meth)acrylic acid, maleic acid, maleic acid anhydride, and fumaric acid, and salts thereof; a nonionic monomer such as (meth)acrylamide, N,N-dimethyl (meth)acrylamide, 2-hydroxyethyl (meth)acrylate, N-methylol (meth)acrylamide, and polyethylene glycol mono(meth)acrylate; an amino group-containing unsaturated monomer such as N,N-diethylaminoethyl (meth)acrylate, N,N-diethylaminopropyl (meth)acrylate, and diethylaminopropyl (meth)acrylamide, and quaternized products thereof; and a sulfonic acid-based monomer such as vinyl sulfonic acid, styrene sulfonic acid, 2-(meth)acrylamide-2-methylpropane sulfonic acid, and 2-(meth)acryloylethanesulfonic acid, and salts thereof. The ethylenically unsaturated monomer may contain at least one (meth)acrylic acid compound selected from the group consisting of (meth)acrylic acid and salts thereof. The ethylenically unsaturated monomer may contain both (meth)acrylic acid and a salt of (meth)acrylic acid. Examples of the salt of α,β-unsaturated carboxylic acid ((meth)acrylic acid or the like) include alkali metal salts (sodium salts, potassium salts, and the like) and alkaline earth metal salts (calcium salts and the like).

The content of the structural unit derived from the (meth)acrylic acid compound may be within the following range based on the total amount of structural units constituting the water-absorbent resin. The content of the structural unit derived from the (meth)acrylic acid compound may be 50 mol % or more, 70 mol % or more, 90 mol % or more, 95 mol % or more, 97 mol % or more, or 99 mol % or more. The structural units constituting the water-absorbent resin may be substantially an aspect composed of the structural unit derived from the (meth)acrylic acid compound (an aspect in which substantially 100 mol % of the structural units constituting the water-absorbent resin are structural units derived from a (meth)acrylic acid compound).

In a case where the water-absorbent resin is in the form of particles, the median particle diameter of the water-absorbent resin may be within the following range. The median particle diameter may be 200 μm or more, 250 μm or more, 300 μm or more, or 340 μm or more. The median particle diameter may be 600 μm or less, 550 μm or less, 500 μm or less, 450 μm or less, 400 μm or less, or 350 μm or less. From these viewpoints, the median particle diameter may be 200 to 600 μm. The median particle diameter can be measured by a method described in Examples to be described below. As the median particle diameter, a measurement value at room temperature can be used.

The water absorption amount of physiological saline of the water-absorbent resin may be 10 g/g or more, 20 g/g or more, 30 g/g or more, 40 g/g or more, 50 g/g or more, or 60 g/g or more. The water absorption amount of physiological saline of the water-absorbent resin may be 80 g/g or less, 70 g/g or less, or 60 g/g or less. From these viewpoints, the water absorption amount of physiological saline of the water-absorbent resin may be 10 to 80 g/g. The water absorption amount can be measured by a method described in Examples to be described below. As the water absorption amount, a measurement value at room temperature can be used.

The silver zeolite is a zeolite in which silver ions are present in pores and can be obtained by the ion exchange of some or all of the ion-exchangeable ions in the zeolite with silver ions. The silver zeolite may contain metal ions other than silver ions. Examples of the metal ions other than silver ions include zinc ions and copper ions.

The average particle diameter of the silver zeolite may be 0.1 μm or more, 0.5 μm or more, 0.8 μm or more, or 1 μm or more. The average particle diameter of the silver zeolite may be 10 μm or less, 5 μm or less, 4 μm or less, 3 μm or less, or 2 μm or less. From these viewpoints, the average particle diameter of the silver zeolite may be 0.1 to 10 μm.

The average particle diameter of the silver zeolite can be measured by, for example, a laser diffraction/scattering method. As the average particle diameter of the silver zeolite, a measurement value at room temperature can be used.

The content of the silver zeolite is preferably within the following range based on the total mass of the water-absorbent resin from the viewpoint of easily improving the deodorant performance and the viewpoint of easily suppressing yellowing over time. The content of the silver zeolite is preferably 50 ppm or more, 100 ppm or more, 150 ppm or more, 200 ppm or more, 250 ppm or more, 300 ppm or more, 350 ppm or more, 400 ppm or more, 450 ppm or more, or 500 ppm or more. The content of the silver zeolite is preferably 1000 ppm or less, 900 ppm or less, 800 ppm or less, 700 ppm or less, 600 ppm or less, or 500 ppm or less. From these viewpoints, the content of the silver zeolite is preferably 50 to 1000 ppm.

The deodorant composition of the present embodiment contains a sulfur compound (a compound including a sulfur atom). The sulfur compound may be present on the surface of the water-absorbent resin and may not be contained in the water-absorbent resin. The sulfur compound may contain an inorganic compound (a compound not including a carbon atom) or may contain an organic compound (a compound including a carbon atom).

Examples of the inorganic compound include peroxosulfuric acid (persulfuric acid. For example, peroxymonosulfuric acid and peroxodisulfuric acid) and peroxosulfate (persulfate. For example, peroxymonosulfate and peroxodisulfate). Examples of the peroxosulfate include sodium salts and potassium salts. The sulfur compound preferably contains peroxosulfate, more preferably contains peroxomonosulfate, and still more preferably contains potassium peroxymonosulfate, from the viewpoint of easily further improving the deodorant performance and the viewpoint of easily suppressing yellowing when 14 days (336 hours) has elapsed from the preparation of the deodorant composition (for example, easily suppressing yellowing when the deodorant composition is retained at a temperature of 70±2° C. and a relative humidity of 90±2% and 14 days (336 hours) has elapsed).

The organic compound may be a compound having a group containing a sulfur atom. Examples of the group containing a sulfur atom include a sulfide group, a disulfide group, a thiocarbamate group, a dithiocarbamate group, and a heterocycle containing a sulfur atom (a thiazole ring, an isothiazole ring, a thiazoline ring, an isothiazoline ring, a benzothiazoline ring, a benzoisothiazoline ring, a thiazolinone ring, an isothiazolinone ring, a benzothiazolinone ring, a benzoisothiazolinone ring, or the like). The compound having a group containing a sulfur atom may have an imidazole ring and/or a benzene ring. To the imidazole ring and/or the benzene ring, a group containing a sulfur atom and/or a group not containing a sulfur atom may bond, and a substituent such as an alkyl group, a hydroxyl group, a carboxyl group, a cyclic group (a benzene ring, a thiazole ring, an isothiazole ring, a thiazoline ring, an isothiazoline ring, a benzothiazoline ring, a benzoisothiazoline ring, a thiazolinone ring, an isothiazolinone ring, a benzothiazolinone ring, a benzoisothiazolinone ring, or the like), a mercapto group, or alkoxy group may bond.

The sulfur compound preferably contains a disulfide compound (a compound having a disulfide group), more preferably contains a thiuram disulfide compound, and still more preferably contains a compound represented by the general formula (1) below, from the viewpoint of easily further improving the deodorant performance and the viewpoint of easily suppressing yellowing when 1 day (24 hours), 3 days (72 hours) or 14 days (336 hours) has elapsed from the preparation of the deodorant composition (for example, easily suppressing yellowing when the deodorant composition is retained at a temperature of 70±2° C. and a relative humidity of 90±2% and 1 day (24 hours), 3 days (72 hours) or 14 days (336 hours) has elapsed).

[Chemical Formula 1]

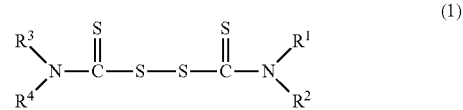

(1)

[In the formula, $R^1$, $R^2$, $R^3$, and $R^4$ each independently represent an alkyl group or an aryl group.]

Examples of the alkyl group in the general formula (1) include a methyl group, an ethyl group, and a propyl group. Examples of the aryl group include a phenyl group. In the compound represented by the general formula (1), at least one selected from the group consisting of $R^1$, $R^2$, $R^3$, and $R^4$ is preferably a methyl group from the viewpoint of easily improving the deodorant performance and the viewpoint of easily suppressing yellowing over time.

The sulfur compound preferably contains a compound having a heterocycle containing a sulfur atom and more preferably contains a compound having a thiazole ring from the viewpoint of easily suppressing yellowing when 1 day (24 hours) or 3 days (72 hours) has elapsed from the preparation of the deodorant composition (for example, easily suppressing yellowing when the deodorant composition is retained at a temperature of 70±2° C. and a relative humidity of 90±2% and 1 day (24 hours) or 3 days (72 hours) has elapsed). The sulfur compound preferably contains a compound having a thiazole ring and an imidazole skeleton, more preferably contains a compound having a thiazole ring and a benzimidazole skeleton, and still more preferably contains thiabendazole (also known as 2-(4-thiazolyl)-benzimidazole), from the viewpoint of easily improving the deodorant performance and the viewpoint of easily suppressing yellowing over time.

The sulfur compound may not have a carboxyl group. The sulfur compound may not have a cyclic structure. The sulfur compound may not have a structural unit derived from a monomer. The number of a sulfur atom in the sulfur compound is preferably 1 to 4, more preferably 2 to 4, and still more preferably 3 or 4, from the viewpoint of easily improving the deodorant performance and the viewpoint of easily suppressing yellowing over time.

The molecular weight of the sulfur compound is preferably within the following range from the viewpoint of easily improving the deodorant performance and the viewpoint of easily suppressing yellowing over time. The molecular weight of the sulfur compound is preferably 80 or more, 100 or more, 120 or more, 130 or more, 140 or more, or 150 or more. The molecular weight of the sulfur compound is preferably 400 or less, 350 or less, 300 or less, 280 or less, 260 or less, or 250 or less. From these viewpoints, the molecular weight of the sulfur compound is preferably 80 to 400. The molecular weight of the sulfur compound may be 160 or more, 180 or more, 200 or more, 220 or more, or 240 or more. The molecular weight of the sulfur compound may be 240 or less, 220 or less, 210 or less, 200 or less, 180 or less, or 160 or less.

In the deodorant composition of the present embodiment, in a case where the deodorant composition contains the water-absorbent resin, the sulfur compound may provide an amount of ammonia generated, which is measured in the following procedures (a1) to (a3), of 1500 ppm or less, 1200 ppm or less, 1000 ppm or less, 800 ppm or less, 500 ppm or less, 450 ppm or less, 400 ppm or less, 200 ppm or less, 100 ppm or less, 50 ppm or less, 30 ppm or less, 10 ppm or less, 5 ppm or less, 3 ppm or less, 2 ppm or less, or 1 ppm or less.

(a1) 25.0 g of urea, 9.0 g of sodium chloride, 0.6 g of magnesium sulfate heptahydrate, 0.7 g of calcium lactate, 4.0 g of potassium sulfate, 2.5 g of ammonium sulfate, and water (for example, distilled water) are mixed to obtain 1000 g of an aqueous solution.

(a2) 30.0 g of the aqueous solution and 1.0 mL of a 10 U/mL urease aqueous solution are mixed to obtain a test solution.

(a3) After 1.0 g of a deodorant composition (a water-absorbent resin composition containing silver zeolite, a sulfur compound, and a water-absorbent resin, in which, based on the total mass of the water-absorbent resin, the content of silver zeolite is 500 ppm, the content of the sulfur compound is 1000 ppm, and the remainder is composed of the water-absorbent resin) is swollen with the test solution (a liquid mixture of 30.0 g of the above-mentioned aqueous solution and 1.0 mL of the urease aqueous solution), the amount of ammonia generated when 24 hours has elapsed (24 hours has elapsed from the swelling) at a temperature of 35±2° C. is measured.

The deodorant composition swollen in (a3) can be retained for 24 hours in, for example, 900 mL of a dry air enclosed in a 2 L bag. The bag enclosing the swollen deodorant composition can be retained at, for example, a temperature of 35±2° C. and a relative humidity of 60±2%.

In the deodorant composition of the first embodiment, the sulfur compound may provide an amount of ammonia generated, which is measured in the following procedures (b1) to (b3), of 2500 ppm or less, 2000 ppm or less, 1500 ppm or less, 1200 ppm or less, 1100 ppm or less, 1000 ppm or less, 800 ppm or less, 700 ppm or less, 600 ppm or less, 500 ppm or less, 300 ppm or less, or 200 ppm or less.

(b1) 25.0 g of urea, 9.0 g of sodium chloride, 0.6 g of magnesium sulfate heptahydrate, 0.7 g of calcium lactate, 4.0 g of potassium sulfate, 2.5 g of ammonium sulfate, and water (for example, distilled water) are mixed to obtain 1000 g of an aqueous solution.

(b2) 30.0 g of the aqueous solution and 1.0 mL of a 30 U/mL urease aqueous solution are mixed to obtain a test solution.

(b3) After the test solution (a liquid mixture of 30.0 g of the above-mentioned aqueous solution and 1.0 mL of the urease aqueous solution) is permeated into entire fluff pulp in an absorber obtained by dispersing 1.875 g of fluff pulp, 0.001 g of silver zeolite, 0.005 g of a sulfur compound, and 0.625 g of fluff pulp in order, the amount of ammonia generated when 24 hours has elapsed (24 hours has elapsed from the permeation) at a temperature of 35±2° C. is measured.

The absorber in (b3) can be retained for 24 hours in, for example, 900 mL of a dry air enclosed in a 2 L bag. The bag enclosing the absorber can be retained at, for example, a temperature of 35±2° C. and a relative humidity of 60±2%.

The content of the sulfur compound is preferably within the following range based on the total mass of the water-absorbent resin from the viewpoint of easily improving the deodorant performance and the viewpoint of easily suppressing yellowing overtime. The content of the sulfur compound is preferably 100 ppm or more, 200 ppm or more, 300 ppm or more, 400 ppm or more, 500 ppm or more, 600 ppm or more, 700 ppm or more, 800 ppm or more, 900 ppm or more, or 1000 ppm or more. The content of the sulfur compound is preferably 3000 ppm or less, 2500 ppm or less, 2000 ppm or less, 1500 ppm or less, 1200 ppm or less, or 1000 ppm or less. From these viewpoints, the content of the sulfur compound is preferably 100 to 3000 ppm.

The total amount of the silver zeolite and the sulfur compound is preferably within the following range based on the total mass of the water-absorbent resin from the viewpoint of easily improving the deodorant performance and the viewpoint of easily suppressing yellowing over time. The total amount is preferably 150 ppm or more, 200 ppm or more, 300 ppm or more, 400 ppm or more, 500 ppm or more, 600 ppm or more, 700 ppm or more, 800 ppm or more, 900 ppm or more, or 1000 ppm or more. The total amount is preferably 5000 ppm or less, 4000 ppm or less, 3000 ppm or less, 2500 ppm or less, 2000 ppm or less, 1500 ppm or less, 1200 ppm or less, or 1000 ppm or less. From these viewpoints, the total amount is preferably 150 to 5000 ppm.

The content of the sulfur compound is preferably within the following range with respect to 100 parts by mass of the silver zeolite from the viewpoint of easily improving the deodorant performance and the viewpoint of easily suppressing yellowing over time. The content of the sulfur compound is preferably 10 parts by mass or more, 20 parts by mass or more, 30 parts by mass or more, 50 parts by mass or more, 80 parts by mass or more, 100 parts by mass or more, 120 parts by mass or more, 150 parts by mass or more, 180 parts by mass or more, or 200 parts by mass or more. The content of the sulfur compound is preferably 2000 parts by mass or less, 1500 parts by mass or less, 1000 parts by mass or less, 800 parts by mass or less, 500 parts by mass or less, 300 parts by mass or less, or 200 parts by mass or less. From these viewpoints, the content of the sulfur compound is preferably 10 to 2000 parts by mass, more preferably 50 to 500 parts by mass, and still more preferably 100 to 300 parts by mass.

The deodorant composition of the present embodiment may contain, as other additive, a gel stabilizer; inorganic particles of a flowability improver (lubricant), or the like. Examples of the inorganic particles include silica particles such as amorphous silica.

An absorber of the present embodiment contains the deodorant composition of the present embodiment. That is, in the absorber of the present embodiment, a portion where the silver zeolite and the sulfur compound come into contact with each other (for example, a portion where the silver zeolite and the sulfur compound are present in a mixture form) is present somewhere in the absorber. For example, the sulfur compound may come into contact with the silver zeolite attached to a fibrous substance to be described below, and the silver zeolite may come into contact with the sulfur compound attached to the fibrous substance.

The content of the silver zeolite is preferably within the following range based on the total mass of the absorber from the viewpoint of easily improving the deodorant performance. The content of the silver zeolite is preferably 10 ppm or more, 50 ppm or more, 70 ppm or more, 90 ppm or more, 120 ppm or more, 150 ppm or more, 180 ppm or more, 200 ppm or more, 250 ppm or more, or 300 ppm or more. The content of the silver zeolite is preferably 1000 ppm or less, 900 ppm or less, 800 ppm or less, 700 ppm or less, 600 ppm or less, or 500 ppm or less. From these viewpoints, the content of the silver zeolite is preferably 10 to 1000 ppm.

The content of the sulfur compound is preferably within the following range based on the total mass of the absorber from the viewpoint of easily improving the deodorant performance. The content of the sulfur compound is preferably 30 ppm or more, 60 ppm or more, 90 ppm or more, 120 ppm or more, 150 ppm or more, 200 ppm or more, 250 ppm or more, 300 ppm or more, 400 ppm or more, or 500 ppm or more. The content of the sulfur compound is preferably 3000 ppm or less, 2500 ppm or less, 2000 ppm or less, 1800 ppm or less, 1500 ppm or less, 1000 ppm or less, 800 ppm or less, or 700 ppm or less. From these viewpoints, the content of the sulfur compound is preferably 30 to 3000 ppm or 30 to 2000 ppm.

The total amount of the silver zeolite and the sulfur compound is preferably within the following range based on the total mass of the absorber from the viewpoint of easily improving the deodorant performance. The total amount is preferably 40 ppm or more, 100 ppm or more, 150 ppm or more, 200 ppm or more, 250 ppm or more, 300 ppm or more, 400 ppm or more, 500 ppm or more, 600 ppm or more, or 800 ppm or more. The total amount is preferably 4000 ppm or less, 3500 ppm or less, 3000 ppm or less, 2500 ppm or less, 2000 ppm or less, 1500 ppm or less, or 1200 ppm or less. From these viewpoints, the total amount is preferably 40 to 4000 ppm or 40 to 3000 ppm.

The absorber of the present embodiment may contain a fibrous substance and is, for example, a mixture containing the deodorant composition and the fibrous substance. For example, the structure of the absorber may be a structure in which the deodorant composition and the fibrous substance are uniformly mixed, may be a structure in which the deodorant composition is sandwiched between the fibrous substances formed in the form of a sheet or a layer, or may be other structures.

Examples of the fibrous substance include finely pulverized wood pulp; cotton; cotton linter; rayon; cellulosic fibers such as cellulose acetate; synthetic fibers such as polyamides, polyesters, and polyolefins; and a mixture of these fibers. As the fibrous substance, hydrophilic fibers can be used.

In order to enhance the morphological retention before and during the use of the absorber, the fibers may be caused to adhere to each other by adding an adhesive binder to the fibrous substance. Examples of the adhesive binder include thermal bonding synthetic fibers, hot melt adhesives, and adhesive emulsions.

Examples of the thermal bonding synthetic fibers include total fusion type binders such as polyethylene, polypropylene, and an ethylene-propylene copolymer; and non-total fusion type binders having a side-by-side or core-sheath structure of polypropylene and polyethylene. In the above-mentioned non-total fusion type binders, only a polyethylene portion can be thermally bonded.

Examples of the hot melt adhesives include mixtures of a base polymer such as an ethylene-vinyl acetate copolymer, a styrene-isoprene-styrene block copolymer, a styrene-butadiene-styrene block copolymer, a styrene-ethylene-butylene-styrene block copolymer, a styrene-ethylene-propylene-styrene block copolymer, and an amorphous polypropylene with a tackifier, a plasticizer, an antioxidant, or the like.

Examples of the adhesive emulsions include polymerization products of at least one monomer selected from the group consisting of methyl methacrylate, styrene, acrylonitrile, 2-ethylhexyl acrylate, butyl acrylate, butadiene, ethylene, and vinyl acetate.

The absorber of the present embodiment may contain silver zeolite, a sulfur compound, or a water-absorbent resin that is different from the constituent component of the deodorant composition of the present embodiment; inorganic particles (excluding silver zeolite. For example, amorphous silica); a pigment; a dye; a fragrance; a sticking agent; or the like.

A shape of the absorber of the present embodiment may be, for example, a sheet shape. A thickness of the absorber (for example, a thickness of a sheet-shaped absorber) may be 0.1 to 20 mm or 0.3 to 15 mm.

In a case where the deodorant composition contains a water-absorbent resin, the content of the deodorant composition in the absorber is preferably 2% to 95% by mass, 10% to 80% by mass, or 20% to 60% by mass with respect to a total of the deodorant composition and the fibrous substance from the viewpoint of easily obtaining sufficient absorption characteristics. In a case where the deodorant composition does not contain a water-absorbent resin, the content of the deodorant composition in the absorber is preferably 0.01% to 1% by mass, 0.1% to 0.8% by mass, or 0.2% to 0.5% by mass with respect to the total of the deodorant composition and the fibrous substance from the viewpoint of easily obtaining sufficient absorption characteristics.

The content of the deodorant composition in the absorber is preferably 100 to 1000 g, 150 to 800 g, or 200 to 700 g per 1 $m^2$ of the absorber from the viewpoint of easily obtaining sufficient absorption characteristics. The content of the fibrous substance in the absorber is preferably 50 to 800 g, 100 to 600 g, or 150 to 500 g per 1 $m^2$ of the absorber from the viewpoint of easily obtaining sufficient absorption characteristics.

An absorbent article of the present embodiment includes the absorber of the present embodiment. Examples of other constituents (for example, constituent members) of the absorbent article of the present embodiment include a deodorant composition containing silver zeolite and a sulfur compound (a deodorant composition that is not contained in the absorber); a core wrap that retains the shape of the absorber and prevents the falloff or flow of the constituent of the absorber; a liquid permeable sheet disposed in the outermost part on a side on which a liquid to be absorbed infiltrates; and a liquid impermeable sheet disposed in the outermost part on a side opposite to the side on which a liquid to be absorbed infiltrates. The deodorant composition in the absorber of the absorbent article of the present embodiment may contain a water-absorbent resin or may not contain a water-absorbent resin. For example, the absorbent article of the present embodiment may include an absorber containing a deodorant composition that does not contain a water-absorbent resin and a member that contains a water-absorbent resin. That is, the absorbent article of the present embodiment may contain a water-absorbent resin, and, in the absorbent article of the present embodiment, the water-absorbent resin may be present at a position different from those of the silver zeolite and the sulfur compound in the deodorant composition. Examples of the absorbent article include diapers (for example, paper diapers), toilet training pants, incontinence pads, sanitary materials (sanitary products and the like), sweat pads, pet sheets, portal toilet members, and animal excrement treatment materials.

FIG. 1 is a cross-sectional view showing an example of the absorbent article. An absorbent article 100 shown in FIG. 1 includes an absorber 10, core wraps 20a and 20b, a liquid permeable sheet 30, and a liquid impermeable sheet 40. In the absorbent article 100, the liquid impermeable sheet 40, the core wrap 20b, the absorber 10, the core wrap 20a, and the liquid permeable sheet 30 are laminated in this order. In FIG. 1, there is a portion shown to have a gap between members, but the members may be in close contact with each other with no gap therebetween.

The absorber 10 has water-absorbent resin particles 10a composed of a water-absorbent resin composition and a fiber layer 10b containing a fibrous substance. The water-absorbent resin particles 10a are dispersed in the fiber layer 10b.

The core wrap 20a is disposed on one surface side of the absorber 10 (on an upper side of the absorber 10 in FIG. 1) in a state of being in contact with the absorber 10. The core wrap 20b is disposed on the other surface side of the absorber 10 (on a lower side of the absorber 10 in FIG. 1) in a state of being in contact with the absorber 10. The absorber 10 is disposed between the core wrap 20a and the core wrap 20b. Examples of the core wraps 20a and 20b include tissues, non-woven fabrics, woven fabrics, synthetic resin films having liquid permeation holes, and net-like sheets having meshes. The core wrap 20a and the core wrap 20b each have, for example, a main surface having the same size as that of the absorber 10.

The liquid permeable sheet 30 is disposed in the outermost part on a side on which a liquid to be absorbed infiltrates. The liquid permeable sheet 30 is disposed on the core wrap 20a in a state of being in contact with the core wrap 20a. Examples of the liquid permeable sheet include non-woven fabrics composed of a synthetic resin such as polyethylene, polypropylene, polyester, or polyamide, and porous sheets. The liquid impermeable sheet 40 is disposed in the outermost part on a side opposite to the liquid permeable sheet 30 in the absorbent article 100. The liquid impermeable sheet 40 is disposed below the core wrap 20b in a state of being in contact with the core wrap 20b. Examples of the liquid impermeable sheet 40 include sheets composed of a synthetic resin such as polyethylene, polypropylene, or polyvinyl chloride, and sheets composed of a composite material of these synthetic resins and a non-woven fabric. The liquid permeable sheet 30 and the liquid impermeable sheet 40 each have, for example, a main surface wider than the main surface of the absorber 10, and outer edges of the liquid permeable sheet 30 and the liquid impermeable sheet 40 each extend around the absorber 10 and the core wraps 20a and 20b.

A magnitude relationship among the absorber 10, the core wraps 20a and 20b, the liquid permeable sheet 30, and the liquid impermeable sheet 40 is not particularly limited and is appropriately adjusted according to the use or the like of the absorbent article. Furthermore, a method of retaining the shape of the absorber 10 using the core wraps 20a and 20b is not particularly limited. The absorber may be wrapped with a plurality of the core wraps as shown in FIG. 1 or the absorber may be wrapped with one core wrap.

The absorber may be caused to adhere to a top sheet. In a case where the absorber is sandwiched or covered with the core wraps, it is preferable that at least the core wrap and the top sheet are caused to adhere to each other, and it is more preferable that the core wrap and the absorber are caused to adhere to each other in addition to the adhesion of the core wrap and the top sheet. Examples of an adhesion method of the absorber include a method of causing the absorber to adhere by applying a hot melt adhesive to the top sheet in predetermined intervals in a striped shape, a spiral shape, or the like in a width direction; a method of causing the absorber to adhere using a water-soluble binder such as starch, carboxymethyl cellulose, polyvinyl alcohol, polyvinylpyrrolidone, or other water-soluble polymers. In addition, in a case where the absorber contains thermal bonding synthetic fibers, a method of causing the absorber to adhere by the thermal bonding of the thermal bonding synthetic fibers may be adopted.

According to the present embodiment, it is possible to provide a liquid absorbing method using the deodorant composition, absorber, or absorbent article of the present embodiment. The liquid absorbing method of the present embodiment includes a step of bringing a liquid to be absorbed into contact with the deodorant composition, absorber, or absorbent article of the present embodiment. According to the present embodiment, it is possible to provide the use of the deodorant composition, the absorber, and the absorbent article for liquid absorption. According to the present embodiment, it is also possible to provide a method for suppressing yellowing of a deodorant composition (water-absorbent resin composition) using a deodorant composition containing silver zeolite and a sulfur compound. The method for suppressing yellowing of a deodorant composition of the present embodiment can suppress yellowing by use of a sulfur compound or the adjustment of the content of the sulfur compound.

According to the present embodiment, it is possible to provide a method for producing an absorber using the above-mentioned deodorant composition. The method for producing an absorber of the present embodiment includes an absorber preparation step of obtaining an absorber using the above-mentioned deodorant composition. In the absorber preparation step, an absorber may be obtained using the deodorant composition and a fibrous substance. The method for producing an absorber of the present embodiment may include a deodorant composition preparation step of obtaining the above-mentioned deodorant composition before the absorber preparation step.

According to the present embodiment, it is possible to provide a method for producing an absorbent article using the above-mentioned absorber. The method for producing an absorbent article of the present embodiment includes an absorbent article preparation step of obtaining an absorbent article using the above-mentioned absorber. In the absorbent article preparation step, an absorbent article may be obtained using the absorber and other constituent of the absorbent article. The method for producing an absorbent article of the present embodiment may include a step of obtaining an absorber by the above-mentioned method for producing an absorber before the absorbent article preparation step.

EXAMPLES

Hereinafter, contents of the present invention will be described in further detail using examples and comparative examples, but the present invention is not limited to the following examples.

Experiment A

<Preparation of Deodorant Composition>

Example A1

0.010 g of ZEOMIC HD10N (manufactured by Sinanen Zeomic Co., Ltd., silver zeolite containing a silver ion and a zinc ion (synthetic zeolite), average particle diameter of 1 to 2 µm) was added to 20 g of a water-absorbent resin (manufactured by Sumitomo Seika Chemical Co., Ltd., AQUA KEEP SA60S, a crosslinking polymer having a structural unit derived from a partially neutralized acrylic acid, water absorption amount of physiological saline of 60 g/g, median particle diameter of 342 μm) and then dry-blending was performed for 15 minutes. Subsequently, 0.020 g of potassium peroxymonosulfate was added thereto and then dry-blending was performed for 30 minutes to obtain a particulate deodorant composition. The content of the silver zeolite was 500 ppm based on the total mass of the water-absorbent resin, and the content of the potassium peroxymonosulfate was 1000 ppm based on the total mass of the water-absorbent resin.

The above-mentioned dry blending was performed by the following method. First, each material to be mixed was injected into a container having an inner capacity of 1 L at a predetermined ratio. The materials in the container were mixed by rotating the materials using a cross rotary mixer manufactured by Meiwa Industry for the above-mentioned time under the conditions of a rotating rotation speed of 50 rpm and a revolving rotation speed of 50 rpm.

The water absorption amount of physiological saline of the water-absorbent resin was measured in the following procedure. That is, 500 g of physiological saline was weighed in a beaker having a capacity of 500 mL. Subsequently, 2.0 g of the water-absorbent resin was dispersed in the physiological saline while stirring the physiological saline at 600 rpm using a magnetic stirrer bar (8 mmφ×30 mm, with no ring) such that no lumps were generated. The mixture was left to stand for 60 minutes in a stirred state, and the water-absorbent resin was sufficiently swollen to obtain a swollen gel. The mass Wa [g] of a standard sieve having an opening of 75 μm was measured. The contents in the beaker were filtered using this standard sieve, and the filtrate was left to stand for 30 minutes in a state where the standard sieve was tilted such that an inclination angle became approximately 300 with respect to the horizontal, thereby filtering excess water. The mass Wb [g] of the sieve including the swollen gel was measured, and the water absorption amount [g/g] of the physiological saline was obtained from the following formula.

Water absorption amount of physiological saline=
($Wb-Wa$)/2.0

The median particle diameter of the water-absorbent resin was measured in the following procedure. That is, JIS standard sieves were combined in the order of a sieve having an opening of 850 μm, a sieve having an opening of 600 μm, a sieve having an opening of 500 μm, a sieve having an opening of 425 μm, a sieve having an opening of 300 μm, a sieve having an opening of 250 μm, a sieve having an opening of 150 μm, and a tray from the top. 5 g of the water-absorbent resin was classified using a continuous fully automatic sonic vibration type sieving measuring instrument (robot shifter RPS-205, manufactured by Seishin Enterprise Co., Ltd.). After the classification, the mass of particles remaining on each sieve was calculated as a mass percentage with respect to the total amount, and the particle size distribution was obtained. Regarding this particle size distribution, the particles on the sieves were integrated in descending order of the particle diameters, thereby plotting a relationship between the openings of the sieves and the integrated value of the mass percentages of the particles on the sieves on logarithmic probability paper. The plotted points on the probability paper were connected with straight lines, thereby obtaining a particle diameter corresponding to 50% by mass of the cumulative mass percentage as the median particle diameter.

Example A2

A particulate deodorant composition was obtained in the same manner as in Example A1 except that tetramethylthiuram disulfide was used instead of potassium peroxymonosulfate. The content of the silver zeolite was 500 ppm based on the total mass of the water-absorbent resin, and the content of the tetramethylthiuram disulfide was 1000 ppm based on the total mass of the water-absorbent resin.

Example A3

A particulate deodorant composition was obtained in the same manner as in Example A1 except that thiabendazole was used instead of potassium peroxymonosulfate. The content of the silver zeolite was 500 ppm based on the total mass of the water-absorbent resin, and the content of the thiabendazole was 1000 ppm based on the total mass of the water-absorbent resin.

Comparative Example A1

A particulate deodorant composition was obtained in the same manner as in Example A1 except that potassium peroxymonosulfate was not used. The content of the silver zeolite was 500 ppm based on the total mass of the water-absorbent resin.

Reference Example A1

A water-absorbent resin (manufactured by Sumitomo Seika Chemical Co., Ltd., AQUA KEEP SA60S, water absorption amount of physiological saline of 60 g/g, median particle diameter of 342 μm) was used as it was.
<Ammonia Deodorant Test>

25.0 g of urea, 9.0 g of sodium chloride, 0.6 g of magnesium sulfate heptahydrate, 0.7 g of calcium lactate, 4.0 g of potassium sulfate, 2.5 g of ammonium sulfate, and distilled water were mixed to dissolve the individual components, thereby preparing a total of 1000 g of artificial urine.

1.0 mL of urease (manufactured by Merck & Co., Inc., derived from Jack bean, 50% glycerin solution, 1000 U/mL) was diluted with distilled water to a total of 100 mL to prepare 10 U/mL of a urease aqueous solution.

30.0 g of the above-mentioned artificial urine and 1.0 mL of the above-mentioned urease aqueous solution were mixed, thereby preparing a test solution. Subsequently, 1.0 g of the sample (deodorant composition) was put into a sterile petri dish (inner diameter of 88 mm), and then the above-mentioned test solution was added to swell the sample. After the addition of the test solution, the petri dish was promptly stored in a 2 L Tedlar bag to enclose the sample, and the air in the bag was removed. After that, 900 mL (total amount) of a dry air that had passed through an activated carbon tank was added into the bag using a glass syringe (constant humidity glass syringe, 200 mL, manufactured by Tsuji Seisakusho Co., Ltd.).

The 2 L Tedlar bag enclosing the swollen sample was stored for 24 hours in a desktop-type constant temperature and humidity chamber set to a temperature of 35±2° C. and a relative humidity of 60±2%. After that, the amount of ammonia generated was measured using a gas-detecting tube (manufactured by Gastec Corporation, detecting tube: 3 types of ammonia 3 L, 3La, and 3M). The results are shown in Table 1.
<Evaluation of Yellow Index>

2.0 g of the sample (deodorant composition) was put into a glass measurement container (cylindrical, inner diameter of 3 cm). In order for the calculation of the yellow index of the sample, X, Y, and Z, which are the tristimulus values of a color measurement colorimeter, were measured with a corrected colorimeter (Color Meter ZE6000, manufactured by Nippon Denshoku Industries Co., Ltd.) using a standard white plate. Based on the measurement results of X, Y and Z (tristimulus values), an initial stage value of the yellow index was obtained from the following formula (A). The results are shown in Table 1.

$$\text{Yellow index}=100\times(1.2769\times X-1.0592\times Z)/Y \tag{A}$$

A test regarding the coloring of the sample over time was performed in the following procedure. First, 2.0 g of a sample was uniformly put into a glass container (cylindrical, inner diameter of 3 cm, depth of 1 cm). The container was stored in a desktop-type constant temperature and humidity chamber set to a temperature of 70±2° C. and a relative humidity of 90±2% for 1 day, 3 days, or 14 days. After the day(s) had elapsed, the container was taken out from the constant temperature and humidity chamber and left to stand for a while to cool to room temperature. After that, the yellow index was obtained in the same procedure as described above using the total amount of the sample. The results are shown in Table 1.

Comparative Example B1

An absorber was obtained in the same manner as in Example B1 except that potassium peroxymonosulfate was not used.

<Ammonia Deodorant Test>

25.0 g of urea, 9.0 g of sodium chloride, 0.6 g of magnesium sulfate heptahydrate, 0.7 g of calcium lactate, 4.0 g of potassium sulfate, 2.5 g of ammonium sulfate, and distilled water were mixed to dissolve the individual components, thereby preparing a total of 1000 g of artificial urine.

3.0 mL of urease (manufactured by Merck & Co., Inc., derived from Jack bean, 50% glycerin solution, 1000 U/mL) was diluted with distilled water to a total of 100 mL to prepare 30 U/mL of a urease aqueous solution.

30.0 g of the above-mentioned artificial urine and 1.0 mL of the above-mentioned urease aqueous solution were mixed, thereby preparing a test solution. Subsequently, 30 mL of this test solution was injected into the above-mentioned petri dish, and the test solution was permeated into

TABLE 1

| | Silver zeolite | Sulfur compound | Water-absorbent resin | Ammonia deodorant test [ppm] | Yellow index 0 day | Yellow index 1 day | Yellow index 3 days | Yellow index 14 days |
|---|---|---|---|---|---|---|---|---|
| Example A1 | Used | Potassium peroxymonosulfate | Used | 1 | 8 | 24 | 25 | 28 |
| Example A2 | Used | Tetramethylthiuram disulfide | Used | 1 | 7 | 7 | 8 | 28 |
| Example A3 | Used | Thiabendazole | Used | 460 | 8 | 15 | 21 | 34 |
| Comparative Example A1 | Used | Not used | Used | 1800 | 8 | 24 | 25 | 31 |
| Reference Example A1 | Not used | Not used | Used | 2300 | 5 | 5 | 12 | 21 |

Experiment B

Preparation of Absorber

Example B1

1.875 g of fluff pulp was uniformly dispersed in a range of 60 mm×60 mm in a sterile petri dish (inner diameter: 88 mm). Subsequently, 0.001 g of ZEOMIC HD10N (manufactured by Sinanen Zeomic Co., Ltd., silver zeolite containing a silver ion and a zinc ion (synthetic zeolite), average particle diameter of 1 to 2 μm) was scattered near the center of the sterile petri dish, and then 0.005 g of potassium peroxymonosulfate (sulfur compound) was scattered, thereby disposing a mixture on the fluff pulp. 0.625 g of fluff pulp was scattered on this mixture, thereby obtaining an absorber (pulp total use amount: 2.5 g).

Example B2

An absorber was obtained in the same manner as in Example B1 except that tetramethylthiuram disulfide was used instead of potassium peroxymonosulfate.

Example B3

An absorber was obtained in the same manner as in Example B1 except that thiabendazole was used instead of potassium peroxymonosulfate.

the entire fluff pulp of the absorber. After the injection of the test solution, the petri dish was promptly stored in a 2 L Tedlar bag to enclose the absorber, and the air in the bag was removed. After that, 900 mL (total amount) of a dry air that had passed through an activated carbon tank was added into the bag using a glass syringe (constant humidity glass syringe, 200 mL, manufactured by Tsuji Seisakusho Co., Ltd.).

The 2 L Tedlar bag enclosing the absorber was stored for 24 hours in a desktop-type constant temperature and humidity chamber set to a temperature of 35±2° C. and a relative humidity of 60±2%. After that, the amount of ammonia generated was measured using a gas-detecting tube (manufactured by Gastec Corporation, detecting tube: 3 types of ammonia 3 L, 3La, and 3M). The results are shown in Table 2.

TABLE 2

| | Silver zeolite | Sulfur compound | Water-absorbent resin | Ammonia deodorant test [ppm] |
|---|---|---|---|---|
| Example B1 | Used | Potassium peroxymonosulfate | Not used | 140 |
| Example B2 | Used | Tetramethylthiuram disulfide | Not used | 1100 |

TABLE 2-continued

|  | Silver zeolite | Sulfur compound | Water-absorbent resin | Ammonia deodorant test [ppm] |
|---|---|---|---|---|
| Example B3 | Used | Thiabendazole | Not used | 2000 |
| Comparative Example B1 | Used | Not used | Not used | 3000 |

REFERENCE SIGNS LIST

10: Absorber, 10a: Water-absorbent resin particle, 10b: Fiber layer, 20a, 20b: Core wrap, 30: Liquid permeable sheet, 40: Liquid impermeable sheet, 100: Absorbent article

The invention claimed is:

1. A deodorant composition that is used in an absorbent article, comprising:
   silver zeolite; and
   peroxosulfuric acid.

2. The deodorant composition according to claim 1, wherein the absorbent article contains a water-absorbent resin.

3. A deodorant composition comprising:
   silver zeolite;
   peroxosulfuric acid; and
   a water-absorbent resin.

4. The deodorant composition according to claim 2, wherein the water-absorbent resin has a structural unit derived from an ethylenically unsaturated monomer.

5. The deodorant composition according to claim 4, wherein the ethylenically unsaturated monomer contains at least one selected from the group consisting of acrylic acid, methacrylic acid, and salts of acrylic acid and methacrylic acid.

6. The deodorant composition according to claim 2, wherein a content of the silver zeolite is 50 to 1000 ppm based on a total mass of the water-absorbent resin.

7. The deodorant composition according to claim 2, wherein the deodorant composition exhibits a property of: an amount of ammonia generated, which is measured in the following procedures (A1) to (A3), is 1500 ppm or less, (A1) 25.0 g of urea, 9.0 g of sodium chloride, 0.6 g of magnesium sulfate heptahydrate, 0.7 g of calcium lactate, 4.0 g of potassium sulfate, 2.5 g of ammonium sulfate, and water are mixed to obtain 1000 g of an aqueous solution, (A2) 30.0 g of the aqueous solution and 1.0 mL of a 10 U/mL urease aqueous solution are mixed to obtain a test solution, and (A3) after 1.0 g of the deodorant composition is swollen with the test solution, the amount of ammonia generated when 24 hours has elapsed at a temperature of 35±2° C. is measured.

8. The deodorant composition according to claim 1, further comprising a thiuram disulfide compound.

9. The deodorant composition according to claim 1, wherein a content of the peroxosulfuric acid is 100 to 300 parts by mass with respect to 100 parts by mass of the silver zeolite.

10. An absorber comprising:
the deodorant composition according to claim 1.

11. An absorbent article comprising:
the absorber according to claim 10.

12. The deodorant composition according to claim 3, wherein the water-absorbent resin has a structural unit derived from an ethylenically unsaturated monomer.

13. The deodorant composition according to claim 12, wherein the ethylenically unsaturated monomer contains at least one selected from the group consisting of acrylic acid, meth acrylic acid, and salts of acrylic acid and methacrylic acid.

14. The deodorant composition according to claim 3, wherein a content of the silver zeolite is 50 to 1000 ppm based on a total mass of the water-absorbent resin.

15. The deodorant composition according to claim 3, further comprising a thiuram disulfide compound.

16. The deodorant composition according to claim 3, wherein a content of the peroxosulfuric acid is 100 to 300 parts by mass with respect to 100 parts by mass of the silver zeolite.

17. An absorber comprising:
the deodorant composition according to claim 3.

18. An absorbent article comprising:
the absorber according to claim 17.

* * * * *